United States Patent [19]

Doles et al.

[11] Patent Number: 5,469,252
[45] Date of Patent: Nov. 21, 1995

[54] FIBER OPTIC FLAW DETECTOR AND IDENTIFICATION SYSTEM

[75] Inventors: Joseph E. Doles, Franklin; Robert J. Hadick, Centerville, both of Ohio

[73] Assignee: LaserMike, Inc., Dayton, Ohio

[21] Appl. No.: 215,809

[22] Filed: Mar. 22, 1994

Related U.S. Application Data

[63] Continuation-in-part of Ser. No. 147,930, Nov. 5, 1993.
[51] Int. Cl.$^6$ .................................................. G01N 21/89
[52] U.S. Cl. ........................................ 356/73.1; 356/430
[58] Field of Search .................................. 356/73.1, 243, 356/239, 430

[56] References Cited

U.S. PATENT DOCUMENTS

| | | | |
|---|---|---|---|
| 3,857,637 | 12/1974 | Obenreder | 356/237 X |
| 4,021,217 | 5/1977 | Bondybey et al. | 65/13 |
| 4,131,365 | 12/1978 | Pryor | 356/356 |
| 4,208,126 | 6/1980 | Cheo et al. | 356/51 |
| 4,363,827 | 12/1982 | Eichenbaum | 427/8 |
| 4,638,168 | 1/1987 | Marino et al. | 250/560 |
| 4,638,169 | 1/1987 | Thomann | 250/560 |
| 4,650,322 | 3/1987 | Fejer et al. | 356/73.1 |
| 4,659,937 | 4/1987 | Cielo et al. | 250/560 |
| 4,882,497 | 11/1989 | Inoue et al. | 250/560 |
| 4,924,087 | 5/1990 | Bailey et al. | 356/73.1 |
| 5,015,867 | 5/1991 | Siegel et al. | 250/560 |
| 5,185,636 | 2/1993 | Button et al. | 356/73.1 |
| 5,208,645 | 5/1993 | Inoue et al. | 356/73.1 |
| 5,216,486 | 6/1993 | Sullerot et al. | 356/385 |
| 5,251,001 | 10/1993 | Dave et al. | 356/73.1 |

OTHER PUBLICATIONS

Presby, H. M., "Refractive index and diameter Measurement of unclad optical fibers", *Jou. of the Optical Society of America*, vol. 64, No. 3, Mar. 1974, pp. 280–284.

Watkins, L. S., "Scattering from Olde–Illuminated clad glass fibers for determination of fiber parameters", *Journal of the Optical Society of America*, vol. 64, No. 6, Jun. 1974, pp. 767–772.

*Primary Examiner*—Vincent P. McGraw
*Attorney, Agent, or Firm*—Killworth, Gottman, Hagan & Schaeff

[57] ABSTRACT

A fiber optic flaw detection system and method for detecting flaws in an optical fiber and for identifying the type of flaw as a lump, neckdown or other is provided. Three collimated beams of light rays illuminate the optical fiber substantially orthogonal to a longitudinal axis thereof. Each beam is scattered by a flaw-free optical fiber into an in-plane scattered light segment which is scattered in a radial plane substantially perpendicular to the longitudinal axis of the optical fiber. A flaw in the optical fiber scatters the light rays into an out-of-plane scattered light segment which is outside of the radial plane. A pair of photocells detects the out-of-plane scattered light segment for each of the beams. One photocell detects the portion of the out-of-plane light segment scattered opposite the direction of travel of the optical fiber. The other photocell detects the portion of the out-of-plane scattered light segment scattered toward the direction of travel of the optical fiber. Based on the temporal order of the illumination of the respective photocells, the type of flaw in the optical fiber is determined. The size of the flaw is also determined based on the level of illumination each photocell experiences.

18 Claims, 5 Drawing Sheets

FIBER OPTIC FLAW DETECTOR AND IDENTIFICATION SYSTEM

This is a continuation-in-part of application Ser. No. 08/147,930, filed Nov. 5, 1993, entitled FIBER OPTIC FLAW DETECTOR SYSTEM AND CALIBRATION APPARATUS, the disclosure of which is hereby incorporated by reference.

BACKGROUND OF THE INVENTION

The present invention relates generally to systems for detecting flaws in optical fibers and, more particularly, to a system and method for detecting flaws and for identifying the types of flaws in an optical fiber wherein a beam of collimated light rays illuminates the optical fiber and is acted upon to form a plane when a flawless optical fiber is illuminated. Portions of the beam which are scattered outside of the plane by flaws are monitored to detect and identify those flaws.

Due to their excellent transmission characteristics, optical fibers are being increasingly used as signal carriers not only in communications systems but also in a wide variety of other applications including weapon systems and medical diagnostic instruments. Generally, optical fibers consist of a fiber core surrounded by a fiber cladding which has a lower index of refraction than the fiber core. Within the layers of an optical fiber, nonuniformities may occur as a result of faulty fabrication or improper handling of the fiber. The nonuniformities may include, for example, bubbles, lumps, neckdowns, coating defects, surface contamination, core contamination and the like.

Such nonuniformities may increase the signal losses in the fiber or, in the extreme, completely terminate signal transmission. It is apparent that these deleterious effects of defects or flaws in the optical fiber may result in malfunction of a device in which the fiber is employed. Consequently, optical fibers must be carefully examined to detect and identify any such defects or flaws.

Fiber optic flaw detection systems which direct a laser beam toward an optical fiber and monitor the refraction and diffraction of the laser beam to detect flaws are known in the art. For example, U.S. Pat. No. 4,924,087 issued to Bailey et al. discloses a fiber optic defect detection system wherein the optical fiber to be examined is extended axially through a dish-like structure and illuminated by one or more laser beams directed substantially orthogonal to the fiber axis. For a flaw free optical fiber, the laser beam is scattered by the optical fiber onto a light-absorbing band on an inner surface of the dish as in-plane scattered rays. For an optical fiber having a flaw, a portion of the laser beam is scattered outside the band as out-of-plane scattered rays. Out-of-plane rays which deviate a sufficient amount from the band illuminate an aperture located above the band and are detected as flaws.

Unfortunately, the Bailey et al. flaw detector does not respond to out-of-plane light rays which are scattered below the light-absorbing band such that this detector is at best not as sensitive as possible when detecting flaws which only cause such scattering or predominately scatter rays in that direction. Furthermore, the Bailey et al. flaw detector does not identify the type of flaw, lump or neckdown, which is detected.

U.S. Pat. No. 4,021,217 issued to Bondybey et al. discloses a method for detecting optical fiber defects wherein the off axis scattering of a beam of monochromatic light by the optical fiber is monitored to detect defects. A plurality of light detectors detect the amount of off-axis light diffracted by flaws in the optical fiber and generate signals representative of the flaws. The magnitudes of the generated signals provide an indication of the sizes of detected flaws. However, the Bondybey et al. flaw detector does not distinguish between, for example, a lump or a neckdown, in the optical fiber.

Identifying the type of flaw in an optical fiber can be beneficial in a variety of circumstances. Such information may be of great importance, for instance, to a manufacturer of optical fibers. The manufacturer may correct a defective manufacturing process based partially on the type of flaws present in the optical fiber. Thus, early detection and identification of flaws in the optical fiber may provide invaluable assistance to the manufacturer in correcting the manufacturing process.

Accordingly, a need exists in the art for an improved approach to flaw detection and identification in optical fibers which is fast and reliable, accurately detects flaws, identifies the types of flaws, such as lump or neckdown, and is easy to operate.

SUMMARY OF THE INVENTION

This need is met by the system and method of the present invention for detecting flaws in an optical fiber and for identifying the flaws in the optical fiber. Three collimated beams of light rays illuminate the optical fiber, preferably substantially orthogonal to a longitudinal axis thereof. The optical fiber enters each of the light beams at an entrance point and exits at an exit point generally opposite the entrance point. Segments of the light beams which are scattered by a flaw in the optical fiber are detected by photocells. Specifically, for each of the light beams, one photocell detects light scattered as the flaw enters the light beam and one photocell detects light scattered as the flaw exits the light beam. Based on the temporal order in which the photocells are illuminated, the type of flaw, lump or neckdown, is determined. The size of the flaw may also be determined based on the intensity at which each photocell is illuminated.

In accordance with one aspect of the present invention, a system for detecting a flaw in an optical fiber and for determining the type of the flaw is provided. The system comprises a light source for generating a collimated beam of light rays which illuminate the optical fiber substantially orthogonal to a longitudinal axis thereof. The optical fiber enters the beam at an entrance point and exits the beam at an exit point generally opposite the entrance point. At least a portion of the beam illuminating the optical fiber is scattered by the fiber into an in-plane scattered light segment consisting of light rays which are scattered in a radial plane substantially perpendicular to the longitudinal axis of the optical fiber and an out-of-plane scattered light segment consisting of light rays which are scattered out of the radial plane. The out-of-plane scattered light segment results from flaws in the optical fiber. A light detector assembly detects the out-of-plane scattered light segment of the beam and produces a plurality of flaw signals representative thereof. Based on the flaw signals, an electrical circuit determines the type of flaw in the optical fiber.

The light detector assembly preferably comprises a first photocell for receiving a first portion of the out-of-plane scattered light segment and for generating a lump signal representative thereof. The first portion is scattered out of the radial plane generally toward the side of the beam including the entrance point. A second photocell receives a second portion of the out-of-plane scattered light segment and generates a neckdown signal representative thereof. The second portion being scattered out of the radial plane generally toward the side of the beam including the exit point.

The electrical circuit comprises a time comparison circuit which detects the relative times at which the first and second photocells are illuminated when the flaw passes through the beam based on the lump and neckdown signals. The electrical circuit may further comprise a lump indicator responsive to the time comparison circuit for indicating that the flaw is a lump when the first photocell is illuminated before the second photocell is illuminated. Further, the electrical circuit may comprise a neckdown indicator responsive to the time comparison circuit for indicating that the flaw is a neckdown when the second photocell is illuminated before the first photocell is illuminated.

A position detector may detect the intensity of the in-plane scattered light segment of the beam along the radial plane to determine the position of the optical fiber and indicate the position of the optical fiber. The position detector may comprise a resistive photocell positioned to receive the in-plane scattered light segment for generating first and second position signals representative of deviation in position of the in-plane scattered light segment. A position circuit indicates the position of the optical fiber based on the first and second position signals.

To reduce unwanted ultraviolet light, a bandpass optical filter may be positioned to receive the light scattered by the optical fiber prior to receipt by the light detector assembly. The electrical circuit may include a size detector for determining the size of the flaw based on the signal levels of the plurality of flaw signals.

In accordance with another aspect of the present invention, a system is provided for detecting a flaw in an optical fiber and for identifying the type of flaw. The system comprises a light generator assembly for generating a plurality of beams of collimated light rays for illuminating the optical fiber along a corresponding plurality of light axes. The optical fiber enters each of the beams at an entrance point and exits each of the beams at an exit point generally opposite the entrance point. At least a portion of each of the beams S illuminate the optical fiber and are scattered thereby into an in-plane scattered light segment consisting of light rays which are scattered in a corresponding plane and an out-of-plane scattered light segment consisting of light rays which are scattered out of the plane. The out-of-plane scattered light segment results from flaws in the optical fiber. A plurality of light detector assemblies each of which is associated with a corresponding beam detect the out-of-plane scattered light segment. The light generator assemblies may comprise at least one laser diode for generating the plurality of beams. Each of the light detector assemblies includes a first photocell for receiving a first portion of the out-of-plane scattered light segment and for generating lump signals representative thereof and a second photocell for receiving a second portion of the out-of-plane scattered light segment and for generating neckdown signals representative thereof. The first portion is scattered out of the radial plane generally toward the fiber entrance point of the corresponding beam. The second portion is scattered out of the radial plane generally toward the fiber exit point of the corresponding beam.

To filter ultraviolet light, at least one bandpass optical filter is positioned to receive the light generated by at least one of the beams and scattered by the fiber prior to receipt by a corresponding at least one of the light detector assemblies. An electrical circuit determines the type of the flaw based on the lump and neckdown signals.

The electrical circuit may comprise a size detector circuit for determining the size of the flaw based on the lump and neckdown signals. A time comparison circuit may be included in the electrical circuit for detecting the relative times at which the first and second photocells are illuminated when the flaw passes through the beams based on the lump and neckdown signals.

In accordance with yet another aspect of the present invention, a method for detecting a flaw in an optical fiber and for identifying the type of the flaw is provided. The method comprises the steps of: illuminating the optical fiber with at least one beam of collimated light rays generally orthogonal to a longitudinal axis of the optical fiber, the optical fiber entering and exiting each of the at least one beam at entrance and exit points, respectively, at least a portion of each of the at least one beam being scattered by the optical fiber into an in-plane scattered light segment consisting of light rays which are scattered in a radial plane substantially perpendicular to the longitudinal axis of the optical fiber and an out-of-plane scattered light segment consisting of light rays which are scattered out of the radial plane, the out-of-plane scattered light segment resulting from flaws in. the optical fiber; generating a plurality of flaw signals representative of the out-of-plane scattered light segment for each of the at least one beam; and, determining the type of flaw based on the plurality of flaw signals.

The step of generating a plurality of flaw signals may comprise the steps of: detecting a first portion of the out-of-plane scattered light segment for each of the at least one beam, the first portion being scattered out of the radial plane generally toward the side of the at least one beam which includes the entrance point; generating a lump signal representative of the illumination of the first photocell by the first portion of each of the at least one beam; detecting a second portion of the out-of-plane scattered light segment for each of the at least one beam, the second portion being scattered out of the radial plane generally toward the side of the at least one beam which includes the exit point; and, generating a neckdown signal representative of the illumination of the second portion of the out-of-plane scattered light segment for each of the at least one beam.

The step of determining the type of flaw may comprise the step of indicating that the flaw is a lump when the first photocell is illuminated prior to the second photocell based on the lump and neckdown signals for each of the beams. Further, the step of determining the type of flaw may further comprise the step of indicating that the flaw is a neckdown when the second photocell is illuminated prior to the first photocell based on the lump and neckdown signals for each of the beams.

The method may further comprise the steps of: detecting the intensity of the in-plane scattered light segment along the radial plane of at least one of the beams; and, determining the position of the optical fiber based on the detected intensity along the radial plane.

These and other features and advantages of the present invention will become apparent from the following detailed description, the accompanying drawings and the appended claims.

DETAILED DESCRIPTION OF THE INVENTION

Figure 1:
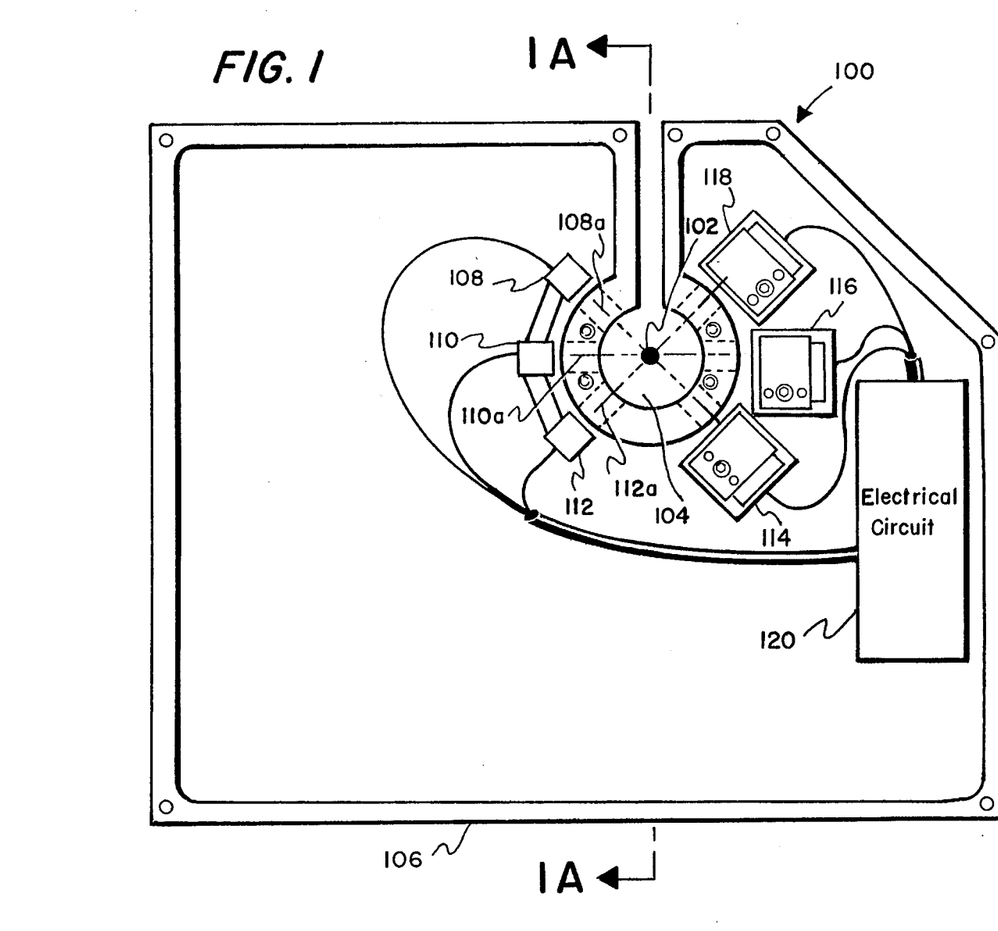
FIG. 1 is a schematic front elevational view of the fiber optic flaw detection and identification system in accordance with the present invention including three collimated beams of light.
Figure 1A:
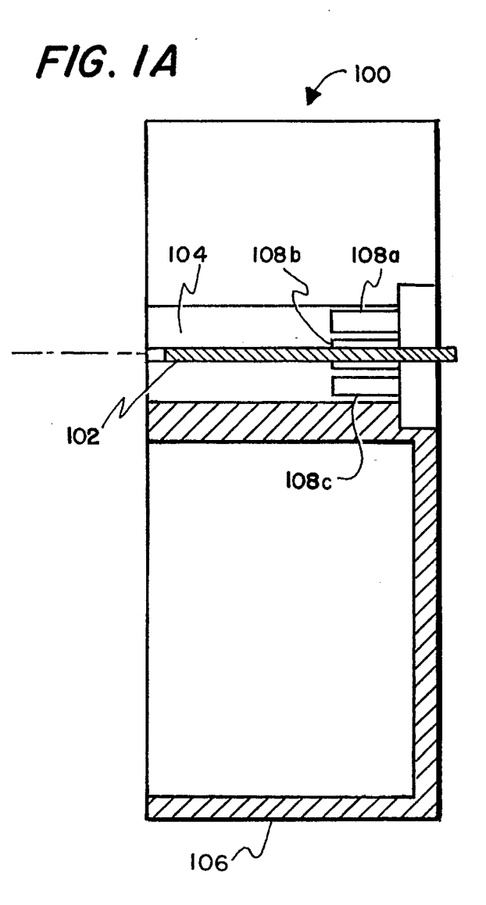
FIG. 1A is a sectional view of the fiber optic flaw detection and identification system taken along line 1A—1A in FIG. 1.

A schematic front elevational view of a system 100 of the present invention for detecting a flaw in an optical fiber 102 and for determining the type of the flaw is shown in FIG. 1 with a front cover removed to expose the interior of the system 100. The optical fiber 102 is translated along its longitudinal axis A through an opening 104 in a housing 106 of the system 100 during testing. Three light sources 108, 110 and 112, which comprise a light generator assembly, generate three collimated beams of light rays 108a, 110a and 112a, respectively, along three axes. The light sources 108, 110 and 112 may be, for example, Hitachi 10 mW HL6714G visible Laser Diodes. The light sources 108, 110 and 112 are powered by a conventional power source (not shown). In the illustrated embodiment, each of the collimated beams 108a, 110a and 112a illuminate the optical fiber 102 substantially orthogonal to the longitudinal axis A of the fiber 102 which is preferred.

As the beams 108a, 110a and 112a traverse the optical fiber 102 and, possibly, encounter flaws, they are scattered. Each of the light sources 108, 110 and 112 is associated with a corresponding light detector assembly 114, 116 and 118 for detecting at least a portion of the scattered light rays emanating from the fiber 102 and for generating a plurality of flaw signals representative of the detected portion of the scattered light rays. An electrical circuit 120 determines whether a flaw is present in the optical fiber 102 and, if so, further identifies the type of flaw based on the flaw signals. The electrical circuit 120 also controls the operation of the light sources 108, 110 and 112.

Although three light sources 108, 110 and 112 are shown in FIG. 1, it should be understood that the present invention may operate using any reasonable number of light sources. Three light sources positioned 45° apart are preferred, however, to ensure that at least one of the beams encounters a flaw in the optical fiber 102 substantially irrespective of the position of the flaw. One skilled in the art will readily comprehend that the beams 108a, 110a and 112a may be generated from one or more light sources. For instance, a single light source may generate a beam of collimated light rays which is divided into three subbeams with each of the three subbeams being directed onto the optical fiber at different angles by appropriately configured mirrors, prisms, optical fibers or other optical elements.

Since each pair of light sources and light detector assemblies are similarly constructed and operate in identical fashion, the structure and operation of only the light source 108 and the light detector assembly 114 will now be described in detail with reference to FIGS. 2A through B. The light source 108 generates the beam 108a of light rays which illuminates the optical fiber 102 substantially orthogonal to the longitudinal axis A thereof. A convex lens 122 is provided on the light source 108 to collimate and focus the beam 108a onto the optical fiber 102.

Figure 2A:
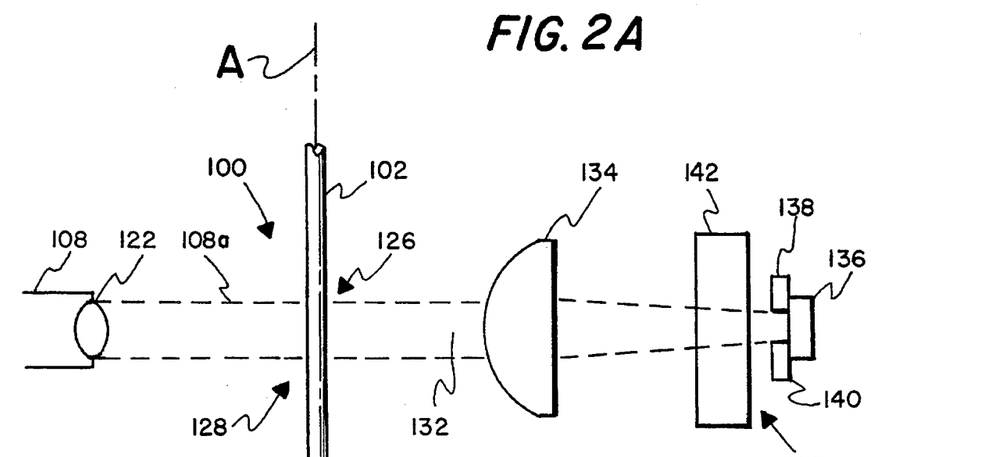
FIGS. 2A and 2B are schematic representations of a single collimated beam of laser light as used in the present invention showing a top view and a side view, respectively.

The optical fiber 102, which is travelling in a direction indicated by arrow 124 in FIG. 2A, enters the collimated beam 108a at an entrance point 126 and exits the collimated beam 108a at an exit point 128 which is generally opposite the entrance point 126. As the beam 108a passes through the optical fiber 102, portions of the beam 108a are scattered, or diffracted.

Figure 2B:
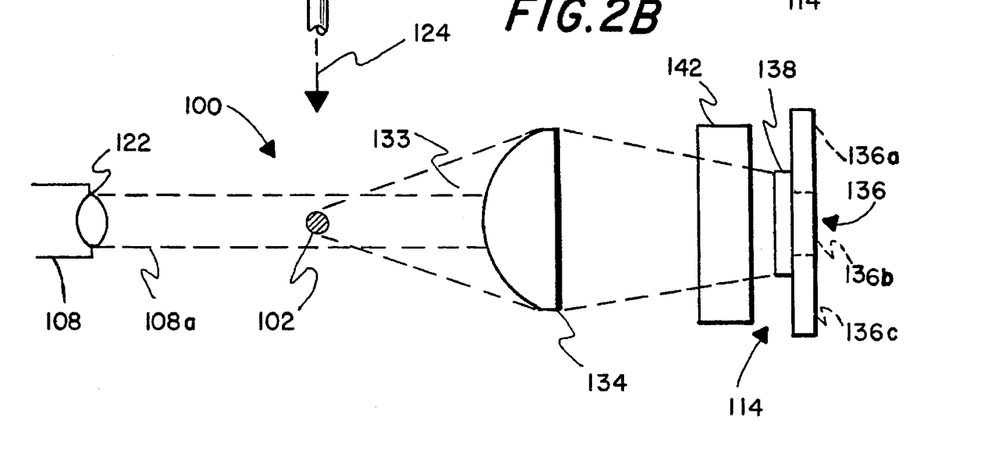

FIGS. 2A and 2B are top and side views, respectively, showing the beam scattering for a flawless optical fiber. The optical fiber 102 scatters a portion of the beam into an in-plane scattered light segment 132 consisting of light rays which are scattered in a radial plane 133 substantially perpendicular to the longitudinal axis A of the optical fiber 102. A plano-convex lens 134 focuses the in-plane scattered light segment onto a position detector 136. The position detector 136, which is described more fully below, monitors the intensity of the in-plane scattered light segment 132 along the radial plane 133 to determine the position of the optical fiber 102 within the collimated beam 108a.

When a flaw is encountered in the optical fiber 102, a portion of the beam 108a is scattered in an out-of-plane scattered light segment consisting of light rays which are scattered out of the radial plane 133. The light detector assembly 114 consisting of first and second photocells 138 and 140 detects the out-of-plane scattered light segment of the beam 108a and produces the flaw signals in response thereto. The electrical circuit 120 determines the type of flaw in the optical fiber 102 based on the flaw signals.

More particularly, a first portion of the out-of-plane scattered light segment is scattered out of said radial plane 133 generally toward the side of the beam 108a including the entrance point 126. The first portion of the out-of-plane scattered light segment is detected by the first photocell 138 which generates a lump signal representative thereof. A second portion of the out-of-plane scattered light segment is scattered out of the radial plane 133 generally toward the side of the beam 108a including the exit point 128. The second photocell 140 detects the second portion of the out-of-plane scattered light segment and generates a neckdown signal representative thereof. It should be understood that first and second photocells 138 and 140 may alternatively be abutted with an opaque beam blocker placed therebetween to intercept the inplane scattered light segment 132.

To reduce errors associated with ambient light in the system 100, a bandpass optical filter 142 is provided for filtering ultraviolet light. The bandpass optical filter 142 is preferably positioned to receive the light scattered by the optical fiber 102 prior to receipt by the light detector assembly 114.

Figure 3A:
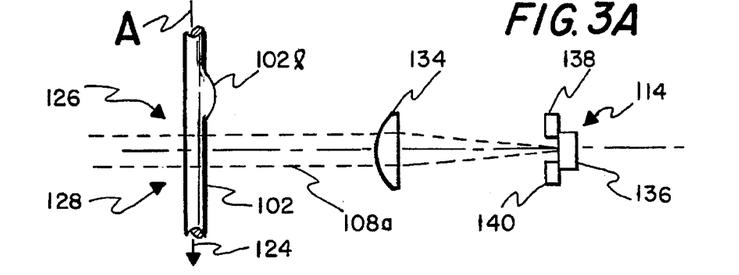
FIGS. 3A through 3D are schematic representations of an optical fiber having a lump flaw traversing a single collimated beam of light.
Figure 3B:
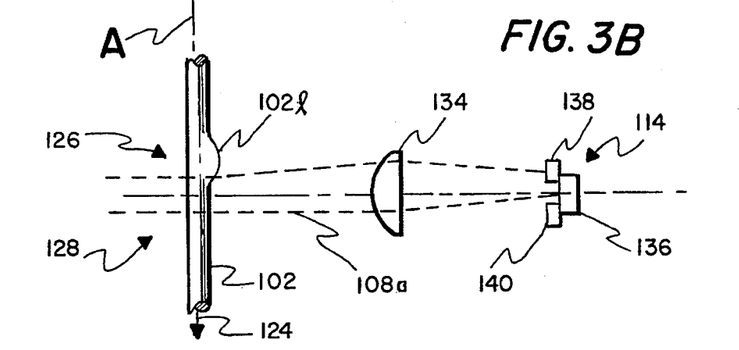

The detection and identification of a lump 102l in the optical fiber 102 by the system 100 will now be described in detail with reference to FIGS. 3A through 3D. As will be apparent to those skilled in the art, a bubble has optical characteristics similar to a neckdown and will be considered a type of neckdown for the subsequent discussion. Prior to encountering the lump 102l, the beam 108a is generally focused in the radial plane 133 and, thus onto the position detector 136, as shown in FIG. 3A. FIG. 3B shows the lump 102l entering the beam 108a at the entrance point 126. The beam 108a is scattered by the initial edge of the lump 102l onto the first photocell 138. At this point, the lump signal generated by the first photocell 138 is at substantially its maximum value and the neckdown signal generated by the second photocell 140 is at its minimum value.

Figure 3C:
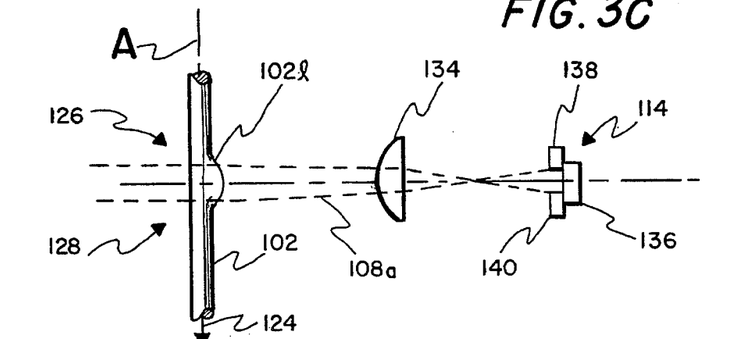
Figure 3D:
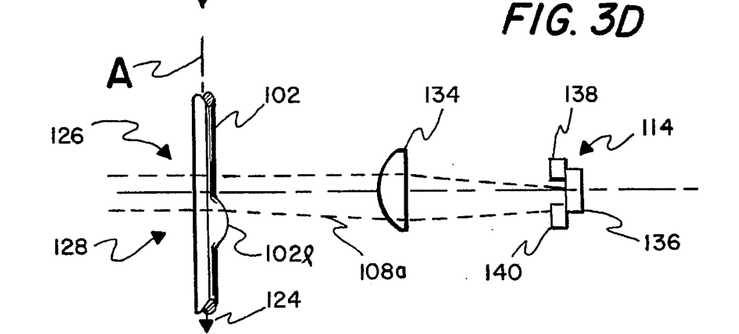

When the lump 102l is generally centered in the beam 108a, as shown in FIG. 3C, the scattered beam 108a strikes the middle of the light detector assembly 114 and illuminates the first and second photocells 138 and 140 substantially equally. When the trailing end of the lump 102l is exiting the beam 108a at the exit point 128, the beam 108a is scattered onto the second photocell 140. At this time, the generated neckdown signal is at its maximum value while the lump signal is at its minimum value. Thus, the maximum value of the lump signal occurs prior to the maximum value of the neckdown signal for a lump.

Figure 4A:
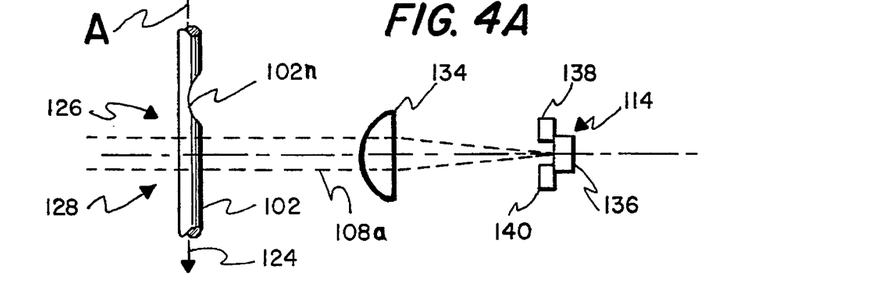
FIGS. 4A through 4D are schematic representations of an optical fiber having a neckdown flaw traversing a single collimated beam of light; and, FIG. 5 is a schematic representation of an electrical circuit and position detector of the fiber optic flaw detection and identification system of the present invention.
Figure 4B:
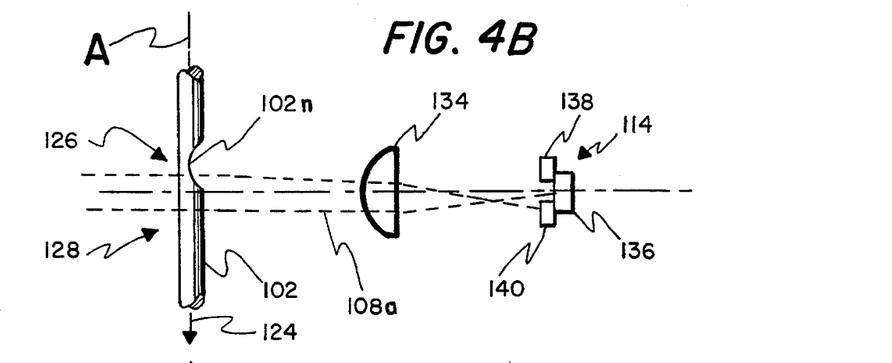
Figure 4C:
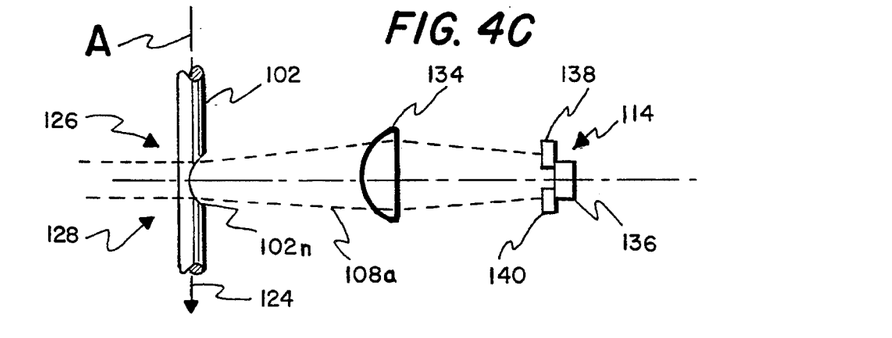
Figure 4D:
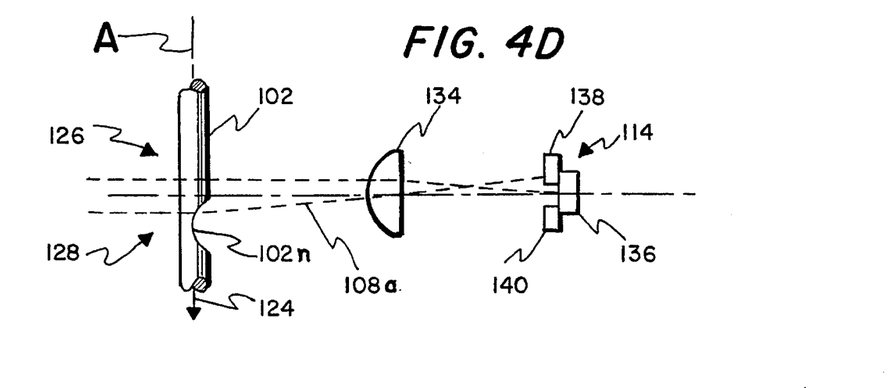

Referring now to FIGS. 4A through 4D, the detection of a neckdown flaw in the optical fiber 102 will now be described. As the neckdown 102n enters the beam 108a, the beam 108a is scattered onto the second photocell 140 as shown in FIG. 4B. Both first and second-photocells 138 and 140 are substantially equally illuminated when the center of the neckdown 102n is centrally positioned in the beam 108a, as shown in FIG. 4C. As the neckdown 102n exits the beam 108a, the first photocell 138 is illuminated. In contrast to the lump 102l, the neckdown 102n causes the second photocell 140 to be illuminated prior to the first photocell 138. Substantially all flaws caused by whatever defect such as coating defects, surface contamination, substrate contamination and any others will result in either a lump or neckdown and will be detected and indicated accordingly. Consequently, by monitoring the temporal order in which first and second photocells 138 and 140 are illuminated, the type of flaw can be determined.

Figure 5:
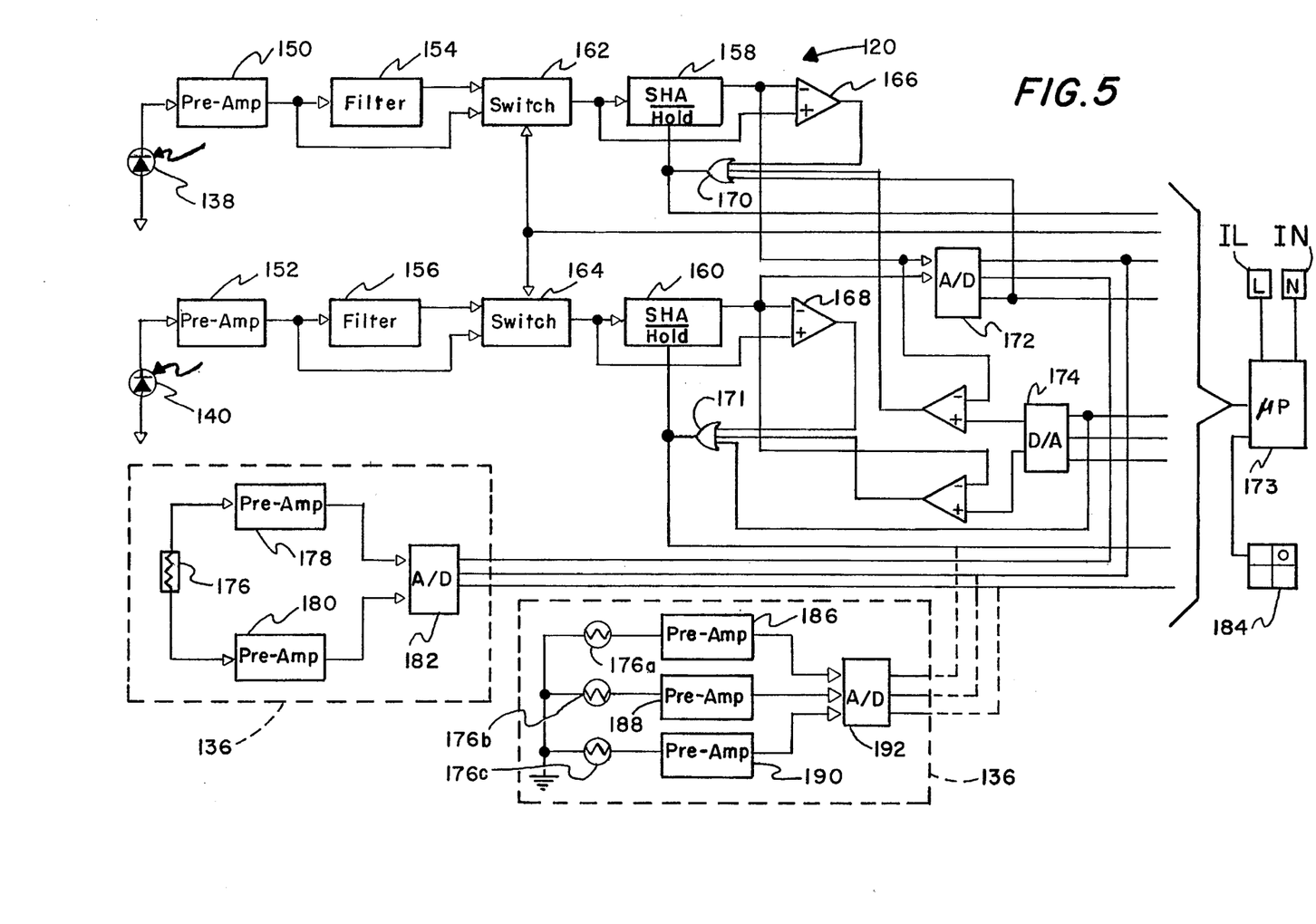

A schematic diagram of the electrical circuit 120 for detecting flaws and for determining the types of flaws from the lump and the neckdown signals generated by the first and second photocells 138 and 140, respectively, is shown in FIG. 5. The electrical circuit 120 receives signals from one pair of photocells. As will be readily comprehended by those skilled in the art, a separate electrical circuit will be provided for each beam of collimated rays illuminating the optical fiber 102. For instance, the system 100 shown in FIG. 1 would have three electrical circuits for detecting a flaw and for detecting and determining the type of flaw. Two alternate embodiments of the circuitry for the position detector 136 for detecting the position of the optical fiber 102 are also shown in FIG. 5. Each of the components shown in FIG. 5 is a conventional electrical device and, therefore, only an overall description of the operation of the electrical circuitry will be given herein.

The electrical circuit 120, or more particularly a time comparison circuit, determines which of the lump signal or the neckdown signal is the first to reach a maximum value. The lump and neckdown signals are generated by the photocells 138 and 140 and amplified by pre-amplifiers 150 and 152, respectively. The amplified lump and neckdown signals are then supplied to respective bandpass filters 154 and 156. Preferably, each of the bandpass filters have a low end cutoff frequency of approximately 60 Hz and a high end cutoff frequency of approximately 1 MHz.

The outputs of the bandpass filters 154 and 156 are received by respective sample and hold amplifiers 158 and 160 via a pair of switches 162 and 164. It should be noted that the switches 158 and 160 are also connected to the respective inputs of the bandpass filters 154 and 156 such that the bandpass filters 154 and 156 can be bypassed during calibration of the system 100. The calibration of the system 100 is described more fully below.

The outputs of the sample and hold amplifiers 158 and 160 and the outputs of the respective bandpass filters 154 and 156 are compared by comparators 166 and 168, respectively. The outputs of the comparators 166 and 168 control the operation of the sample and hold amplifiers 158 and 160 via respective OR gates 170 and 171. More specifically, the sample and hold amplifiers 158 and 160 will continue to sample their inputs as long as the outputs of the filters 154 and 156 are constant or increasing in value. Once the inputs reach a maximum value and begin to decrease, the output of the comparator will switch its respective sample and hold amplifier into a hold mode. As noted above, for a lump or neckdown flaw only one signal will be at a maximum at any given time. The outputs of the sample and hold amplifiers 158 and 160 are also provided to a two channel analog-to-digital (A/D) converter 172 to detect the size of the flaw.

A microprocessor 173, such as a Motorola 68332 TPU, determines the type of flaw as being a lump or a neckdown, and the size of the flaw based on the temporal order of the maximum values of the lump and neckdown signals based on the outputs of the comparators 166 and 168 and the output of the A/D converter 172. Specifically, the microprocessor 173 latches a counter value in response to switching one of the sample and hold amplifiers 1B8 and 160 into its hold mode. As noted above, the switching of one of the sample and hold amplifiers 158 or 160 indicates a maximum value for the corresponding lump or neckdown signal. For a three beam system, separate count values are obtained for each of the beams.

The microprocessor 173 then compares the count values and selects the lowest count value. As should be apparent, the lowest count value corresponds to the maximum signal value which was the first to occur. Based on the determination of which signal first reached a maximum value, the type of flaw is determined. A lump indicator $I_L$ and a neckdown indicator $I_N$ indicate when a lump and a neckdown, respectively, are detected. The sample and hold amplifiers 158 and 160 are reset by the microprocessor 173 via a digital-to-analog (D/A) converter 174.

The size of the flaw may also be determined from the A/D converter 172 outputs by a size detector. The microprocessor 173 reads the output of the channel of the A/D converter 172 corresponding to the signal which first reached a maximum value for each of the three beams. The size of the flaw is determined from the highest A/D converter 172 output detected among the three beams.

The length of a flaw also may be determined by the electrical circuit 120. The outputs of the sample and hold amplifiers 158 and 160 are divided in half by the microprocessor 173 and compared to the lump and neckdown signals, respectively, as generated by the photocells 138 and 140. From this comparison, pulses are created which are located in the middle of the lump and neckdown signals. The length of the flaw is then determined based on the width of the pulses and the line speed of the optical fiber 102. As those skilled in the art will readily comprehend, the speed of the optical fiber may be obtained in any of a variety of conventional manners.

The system 100 of the present invention may be calibrated by the following procedure. As noted above, during calibration, the bandpass filters 154 and 156 are removed from the electrical circuit 120 via the respective switches 162 and 164. An optical fiber is initially placed in the beams 108, 110 and 112 and the microprocessor 173 will determine a baseline voltage at each axis. An optical fiber with a known flaw is then passed into and out of the beams 108, 110 and 112. The microprocessor 173 records the differences between the baseline voltages and the maximum voltages produced for each beam. This information is then stored and used to calibrate future tests.

In a first embodiment, the position detector 136 comprises a single resistive photocell 176 which is positioned to detect variances in the in-plane scattered light segment along the radial plane 133 for one of the beams 108, 110 or 112. A pair of pre-amplifiers 178 and 180 amplify the signals generated by the resistive photocell 176. As will be apparent to those skilled in the art, the respective inputs to the pre-amplifiers 178 and 180 will vary in magnitude based on the uniformity of the in-plane scattered light segment across the resistive photocell 176.

For example, a uniformly varying light centered on the photocell 176 will result in the inputs to the pre-amplifiers 178 and 180 being equal in magnitude. If one half of the resistive photocell 176 detects more light, the input to the pre-amplifier 178 or 180 connected to that half of the photocell 176 will receive a proportionally larger signal. The amplified outputs of the respective pre-amplifiers 178 and 180 are converted into digital signals by an A/D converter 182 for input to the microprocessor 173.

As will be readily apparent to those skilled in the art, a second photocell may be positioned perpendicular to the photocell 176. The second photocell could, therefore, detect the position of the optical fiber in a direction perpendicular to the direction detected by the photocell 176. Further, a display 184, such as a conventional liquid crystal display, may be provided to indicate the position of the optical fiber in the two detected directions.

A second position/power detector embodiment 136' is also illustrated in FIG. 5. In the second position detector embodiment 136', three photocells 176a, 176b and 176c take the place of the single resistive photocell 176 and are positioned to detect variances in the in-plane scattered light segment along the radial plane 133 for one of the beams 108, 110 or 112. Three pre-amplifiers 186, 188 and 190 amplify the signals generated by the photocells 176a, 176b and 176c, respectively, and pass them to an analog-to-digital (A/D) converter 192.

The microprocessor 173 alternately selects the outputs from the A/D converter 192 which are digital representations of the signals generated by the three photocells 176a, 176b and 176c to determine the position of the optical fiber 102 within the corresponding beam and the power of the beam for calibration purposes. For beam position, the signals from the photocells 176a and 176c are selected and compared; and, for beam power the signals from the photocell 176b is selected. The operation of the second position/power detector embodiment 136' is intuitively illustrated by observing that the photocells 176a, 176b and 176c are positioned along segments 136a, 136b and 136c, respectively, of the position detector 136' as illustrated in FIG. 2B.

Here again, a second series of photocells can be positioned perpendicular to the linear array of the photocells 176a, 176b and 176c for determining the position of the optical fiber 102 and displaying that position via the display 184.

During calibration of the system 100, a test optical fiber with a known flaw is repeatedly passed through the collimated beams of light 108a, 110a and 112a. The calibration apparatus disclosed in application Ser. No. 08/147,930, entitled FIBER OPTIC FLAW DETECTOR SYSTEM AND CALIBRATION APPARATUS, which was previously incorporated by reference, is preferably employed to translate the test optical fiber repeatedly through the beams of light 108a, 110a and 112a.

The electrical circuit 120 is initially placed in calibration mode. The bandpass filters 154 and 156, as noted above, are switched out of the electrical circuit 120 in the calibration mode. The size of the flaw and the type of the flaw are entered into the microprocessor 173. The test optical fiber is then repeatedly passed through the beams of light 108a, 110a and 112a. The photocells for each beam of light 108a, 110a and 112a generate signals which are at a baseline level when the flaw-free portion of the test optical fiber is traversing the beams 108a, 110a and 112a and a maximum level when the flaw is traversing the beams. The microprocessor 173 records the difference between the baseline and maximum signal levels for each of the photocells. Subsequent optical fiber tests are then calibrated by the microprocessor 173 based on these recorded signal levels.

Having thus described the invention in detail by way of reference to preferred embodiments thereof, it will be apparent that other modifications and variations are possible without departing from the scope of the invention defined in the appended claims.

What is claimed is:

1. A system for detecting a flaw in an optical fiber and for determining the type of said flaw, said system comprising:

a light source for generating a collimated beam of light rays for illuminating said optical fiber substantially orthogonal to a longitudinal axis thereof, said optical fiber entering said beam at an entrance point and exiting said beam at an exit point generally opposite said entrance point, at least a portion of said beam illuminating said optical fiber being scattered by said fiber into an in-plane scattered light segment consisting of light rays which are scattered in a radial plane substantially perpendicular to said longitudinal axis of said optical fiber and an out-of-plane scattered light segment consisting of light rays which are scattered out of said radial plane, said out-of-plane scattered light segment resulting from flaws in said optical fiber;

a light detector assembly for detecting said out-of-plane scattered light segment of said beam and for producing a plurality of flaw signals representative thereof, said light detector assembly comprising:

a first photocell for receiving a first portion of said out-of-plane scattered light segment and for generating a lump signal representative thereof, said first portion being scattered out of said radial plane generally toward the side of said beam including said entrance point; and a second photocell for receiving a second portion of said out-of-plane scattered light segment and for generating a neckdown signal representative thereof, said second portion being scattered out of said radial plane generally toward the side of said beam including said exit point; and an electrical circuit for determining the type of said flaw in said optical fiber based on said plurality of flaw signals.

2. The system as recited in claim 1 wherein said electrical circuit comprises a time comparison circuit for detecting the relative times at which said first and second photocells are illuminated when said flaw passes through said beam based on said lump and neckdown signals.

3. The system as recited in claim 2 wherein said electrical circuit further comprises a lump indicator responsive to said time comparison circuit for indicating that said flaw is a lump when said first photocell is illuminated before said second photocell is illuminated.

4. The system as recited in claim 2 wherein said electrical circuit further comprises a neckdown indicator responsive to said time comparison circuit for indicating that said flaw is a neckdown when said second photocell is illuminated before said first photocell is illuminated.

5. The system as recited in claim 1 further comprising a bandpass optical filter for filtering ultraviolet light, said bandpass optical filter being positioned to receive light scattered by said optical fiber prior to receipt by said light detector assembly.

6. The system as recited in claim 1 wherein said electrical circuit comprises a size detector for determining the size of said flaw based on the signal levels of said plurality of flaw signals.

7. A system for detecting a flaw in an optical fiber and for determining the type of said flaw, said system comprising:
a light source for generating a collimated beam of light rays for illuminating said optical fiber substantially orthogonal to a longitudinal axis thereof, said optical fiber entering said beam at an entrance point and exiting said beam at an exit point generally opposite said entrance point, at least a portion of said beam illuminating said optical fiber being scattered by said fiber into an in-plane scattered light segment consisting of light rays which are scattered in a radial plane substantially perpendicular to said longitudinal axis of said optical fiber and an out-of-plane scattered light segment consisting of light rays which are scattered out of said radial plane, said out-of-plane scattered light segment resulting from flaws in said optical fiber;
a light detector assembly for detecting said out-of-plane scattered light segment of said beam and for producing a plurality of flaw signals representative thereof;
an electrical circuit for determining the type of said flaw in said optical fiber based on said plurality of flaw signals; and
a position detector for detecting the intensity of said in-plane scattered light segment of said beam along said radial plane to determine the position of said optical fiber and for indicating the position of said optical fiber.

8. The system as recited in claim 7 wherein said position detector comprises:
a resistive photocell positioned to receive said in-plane scattered light segment for generating first and second position signals representative of deviation in position of said in-plane scattered light segment; and
a position circuit for indicating the position of said optical fiber based on said first and second position signals.

9. A system for detecting a flaw in an optical fiber and for identifying the type of said flaw, said system comprising:
a light generator assembly for generating a plurality of beams of collimated light rays for illuminating said optical fiber along a corresponding plurality of light axes, said optical fiber entering each of said beams at an entrance point and exiting each of said beams at an exit point generally opposite said entrance point, at least a portion of each of said beams illuminating said optical fiber and being scattered thereby into an in-plane scattered light segment consisting of light rays which are scattered in a corresponding radial plane and an out-of-plane scattered light segment consisting of light rays which are scattered out of said radial plane, said out-of-plane scattered light segment resulting from flaws in said optical fiber;
a plurality of light detector assemblies each of which is associated with a corresponding beam for detecting said out-of-plane scattered light segment, each of said light detector assemblies including,
a first photocell for receiving a first portion of said out-of-plane scattered light segment and for generating lump signals representative thereof, said first portion being scattered out of said radial plane generally toward said entrance point of said corresponding beam, and
a second photocell for receiving a second portion of said out-of-plane scattered light segment and for generating neckdown signals representative thereof, said second portion being scattered out of said radial plane generally toward said exit point of said corresponding beam;
at least one bandpass optical filter for filtering ultraviolet light, said bandpass optical filter being positioned to receive light generated by at least one of said beams and scattered by said optical fiber prior to receipt by a corresponding at least one of said light detector assemblies; and
an electrical circuit for determining the type of said flaw based on said lump and neckdown signals.

10. The system as recited in claim 9 wherein said electrical circuit further comprises a size detector circuit for determining the size of said flaw based on said lump and neckdown signals.

11. The system as recited in claim 9 wherein said electrical circuit further comprises a time comparison circuit for detecting the relative times at which said first and second photocells are illuminated when said flaw passes through said beams based on said lump and neckdown signals.

12. The system as recited in claim 9 wherein said light generator assembly comprises at least one laser diode for generating said plurality of beams.

13. The system as recited in claim 9 further comprising a plurality of position detectors for detecting the intensity of said in-plane scattered light segments of each of said beams along said radial planes to determine the position of said optical fiber and for indicating the position of said optical fiber.

14. The system as recited in claim 13 wherein each of said position detectors comprises:
a resistive photocell positioned to receive said in-plane scattered light segment for generating first and second position signals representative of deviation in position of said in-plane scattered light segment; and
a position detector for indicating the position of said optical fiber based on said first and second position signals.

15. A method for detecting a flaw in an optical fiber and for identifying the type of said flaw comprising the steps of:
illuminating said optical fiber with at least one beam of collimated light rays generally orthogonal to a longitudinal axis of said optical fiber, said optical fiber entering and exiting each of said at least one beam at entrance and exit points, respectively, at least a portion of each of said at least one beam being scattered by said optical fiber into an in-plane scattered light segment consisting of light rays which are scattered in a radial plane substantially perpendicular to said longitudinal axis of said optical fiber and an out-of-plane scattered light segment consisting of light rays which are scattered out of said radial plane, said out-of-plane scattered light segment resulting from flaws in said optical fiber;

generating a plurality of flaw signals representative of said out-of-plane scattered light segment for each of said at least one beam by performing the steps of:

detecting a first portion of said out-of-plane scattered light segment for each of said at least one beam, said first portion being scattered out of said radial plane generally toward the side of said at least one beam which includes said entrance point;

generating a lump pulse representative of the illumination of said first photocell by said first portion of each of said at least one beam;

detecting a second portion of said out-of-plane scattered light segment for each of said at least one beam, said second portion being scattered out of said radial plane generally toward the side of said at least one beam which includes said exit point; and generating a neckdown signal representative of the illumination of said second portion of said out-of-plane scattered light segment for each of said at least one beam; and determining the type of said flaw based on said plurality of flaw signals.

16. The method as recited in claim 15 wherein the step of determining the type of said flaw further comprises the step of indicating that said flaw is a lump when said first photocell is illuminated prior to said second photocell based on said lump and neckdown signals for each of said beams.

17. The method as recited in claim 15 wherein the step of determining the type of said flaw further comprises the step of indicating that said flaw is a neckdown when said second photocell is illuminated prior to said first photocell based on said lump and neckdown signals for each of said beams.

18. A method for detecting a flaw in an optical fiber and for identifying the type of said flaw comprising the steps of:

illuminating said optical fiber with at least one beam of collimated light rays generally orthogonal to a longitudinal axis of said optical fiber, said optical fiber entering and exiting each of said at least one beam at entrance and exit points, respectively, at least a portion of each of said at least one beam being scattered by said optical fiber into an in-plane scattered light segment consisting of light rays which are scattered in a radial plane substantially perpendicular to said longitudinal axis of said optical fiber and an out-of-plane scattered light segment consisting of light rays which are scattered out of said radial plane, said out-of-plane scattered light segment resulting from flaws in said optical fiber;

generating a plurality of flaw signals representative of said out-of-plane scattered light segment for each of said at least one beam; and determining the type of said flaw based on said plurality of flaw signals;

detecting the intensity of said in-plane scattered light segment along said radial plane of at least one of said beams; and determining the position of said optical fiber based on said detected intensity along said radial plane.

* * * * *